(12) United States Patent
Sunder

(10) Patent No.: US 12,741,155 B2
(45) Date of Patent: Sep. 22, 2026

(54) METHODS AND SYSTEM FOR TREATING HUMAN BODY PART WITH ULTRA-LOW MAGNETO-ELECTRIC FIELD

(71) Applicants: AETHER MINDTECH SOLUTIONS PRIVATE LIMITED, Madhapur (IN); AETHER MINDTECH SOLUTIONS INC., Dover, DE (US)

(72) Inventor: PV Shyam Sunder, Madhapur (IN)

(73) Assignee: AETHER MINDTECH SOLUTIONS INC, Dover, DE (US)

( * ) Notice: Subject to any disclaimer, the term of this patent is extended or adjusted under 35 U.S.C. 154(b) by 864 days.

(21) Appl. No.: 18/054,925

(22) Filed: Nov. 14, 2022

(65) Prior Publication Data

US 2023/0293902 A1 Sep. 21, 2023

(30) Foreign Application Priority Data

Mar. 18, 2022 (IN) ............................ 202241015000

(51) Int. Cl.
*A61N 2/02* (2006.01)
*A61B 5/369* (2021.01)
*A61N 2/00* (2006.01)

(52) U.S. Cl.
CPC .............. *A61N 2/006* (2013.01); *A61B 5/369* (2021.01); *A61N 2/02* (2013.01)

(58) Field of Classification Search
CPC ........... A61N 2/006; A61N 2/02; A61B 5/369
USPC .............................................................. 600/9
See application file for complete search history.

(56) References Cited

U.S. PATENT DOCUMENTS 5,409,445 A * 4/1995 Rubins .................. A61M 21/00 600/27
6,656,137 B1 * 12/2003 Tyldsley ............... A61M 21/00 472/60
8,303,479 B2 * 11/2012 Zapata Perez ........... A61N 2/02 600/13
9,649,502 B2 * 5/2017 Phillips .................. A61N 2/006
2013/0066138 A1 * 3/2013 Rohan .................... A61N 2/006 600/14
2013/0234823 A1 * 9/2013 Kahn ................ G06Q 10/1093 340/3.1
2015/0073313 A1 * 3/2015 Sunnen ................ A61M 21/02 600/27
2018/0110997 A1 * 4/2018 Nedelman ................ A61N 2/02
2019/0060605 A1 * 2/2019 Ramaprakash ....... A61M 21/02

(Continued)

FOREIGN PATENT DOCUMENTS

CN 102228726 A * 11/2011
CN 203736715 U * 7/2014

*Primary Examiner* — Brian L Casler
(74) *Attorney, Agent, or Firm* — Patshegen IP; Moshe Pinchas

(57) ABSTRACT

The embodiments herein achieve methods for treating a human body part using ultra-low magneto-electric field. The method includes acquiring, by at least one of a server (300) and a medical device (100), at least one amplitude, at least one frequency, at least one phase and at least one rhythm. Further, the method includes generating, by at least one of the server (300) and the medical device (100), a plurality of ultra-low magneto-electric field based on the at least one acquired amplitude, at least one acquired frequency, at least one acquired phase and at least one acquired rhythm.

17 Claims, 24 Drawing Sheets

(56) References Cited

U.S. PATENT DOCUMENTS

2023/0270368 A1* 8/2023 Kim .................... A61H 23/008
600/559

* cited by examiner

S1400

S1600

S2000

METHODS AND SYSTEM FOR TREATING HUMAN BODY PART WITH ULTRA-LOW MAGNETO-ELECTRIC FIELD

TECHNICAL FIELD

Embodiments disclosed herein relate to a health management system, and more particularly related to methods and systems for treating a human body part with low frequency magneto-electric field.

BACKGROUND

There are many people across the world facing brain related disorders due to lifestyle. Most of these problems are associated with hyperactivity in brain. A dysregulated brain activity happens due to the influence of various lifestyle factors such as but not limited to social, psychological, environmental, physical and chemical factors affecting human brain in day to day life. The lifestyle associated mental wellbeing is poorly understood and often neglected. Mostly these problems with mild and low are not addressed at all. The current therapies are not addressing the social lifestyle disorders related to mind. The current or existing therapies are not addressing to improve the mental wellbeing in the general public associated with day to day social lifestyle disorders.

OBJECTS

The principal object of embodiments herein is to disclose methods and systems for treating a human body part (e.g., brain part or the like) with low frequency magneto-electric field.

Another object of embodiments herein is to acquire one or more amplitude, one or more frequency, one or more phase and one or more rhythm.

Another object of embodiments herein is to generate a plurality of ultra-low magneto-electric field based on the one or more acquired amplitude, the one or more acquired frequency, the one or more acquired phase and the one or more acquired rhythm.

Another object of embodiments herein is to receive one or more user input, where the one or more user input corresponds to a range of ultra-low magnetic field focused at a head and a neck of the user. The one or more user input can be, for example, but not limited to management of work stress, anxiety, restlessness, lack of focus, irregular sleeping patterns or the like.

Another object of embodiments herein is to generate one or more ultra-low magneto-electric field from the plurality of ultra-low magneto-electric field based on the one or more user input.

Another object of embodiments herein is to pass an electrical signal across a source attached to a media, wherein the media is made of a magnesium and zinc, wherein the source is made of copper and generate a magnetic field in response to passing the electrical signal across the source attached to the media, wherein the magnetic field harmonizes brain cycles/neuronal activity.

Another object of embodiments herein is to provide a medical device (e.g., smart wearable device or the like) to support the user need to tackle day-to-day challenges such as work stress, anxiety, restlessness, lack of focus, irregular sleeping patterns and many more problems associated with hyperactivated brain.

Another object of embodiments herein is to generate ultra-low magneto-electric field with different patterns, very similar to the waves generated in the calming brain. Thus, results in assisting the user brain achieve a harmony state by orchestrating the high frequency (hyperactivated) brain waves.

Another object of embodiments herein is to provide a medical device/house hold device that is easy to use in day-to-day life and safe to use for the long term at reasonable cost without any side effects or adverse effects.

Another object of embodiments herein is to bring any part of agitated brain activity to a normal state with slow, low, rhythmic-Amplitude, Pitch, Phase and Rhythm combination (APPR).

These and other aspects of the embodiments herein will be better appreciated and understood when considered in conjunction with the following description and the accompanying drawings. It should be understood, however, that the following descriptions, while indicating at least one embodiment and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

Embodiments herein are illustrated in the accompanying drawings, throughout which like reference letters indicate corresponding parts in the various figures. The embodiments herein will be better understood from the following description with reference to the drawings, in which.

DETAILED DESCRIPTION

Figure 1A:
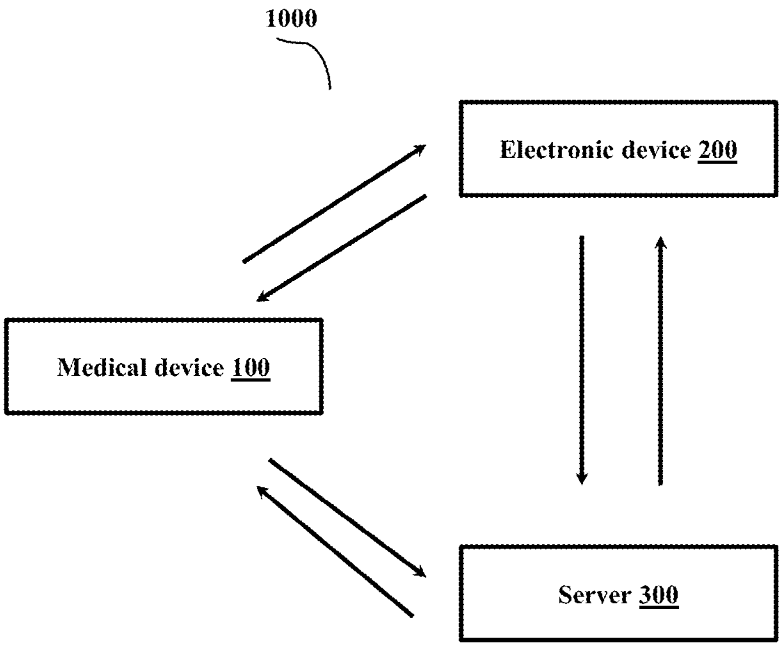
FIG. 1A and FIG. 1B are overviews of a system for treating a human body part using ultra-low magneto-electric field, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The terms "sound file" and "program file" are used interchangeably in the patent disclosure. The terms "media", "ferromagnetic substance", "inductor" and "coil" are used interchangeably in the patent disclosure. The terms "EEG" and "industry standard EEG" are interchangeably in the patent disclosure.

The embodiments herein achieve methods for treating a human body part (e.g., brain part or the like) using ultra-low magneto-electric field. The method includes acquiring, by a server/medical device/electronic device, at least one amplitude, at least one frequency, at least one phase and at least one rhythm. Further, the method includes generating, by the server/medical device, a plurality of ultra-low magneto-electric field based on the at least one acquired amplitude, at least one acquired frequency, at least one acquired phase and at least one acquired rhythm.

The method can be used to generate ultra-low magneto-electric field with different patterns, to modulate biological electrical activity in the human brain. Thus, results in assisting the user brain achieve the normal state by modulating (e.g., neuro-modulating or the like) agitated brain activity. In the proposed method, the medical device (e.g., smart wearable device or the like) can be used to support the user need to tackle day-to-day challenges such as work stress, anxiety, restlessness, lack of focus, irregular sleeping patterns and many more problems associated with hyper activated brain. The medical device is easy to use in day-to-day life, safe to use for the long term at reasonable cost. The medical device can run the sound files for a period of 25-45 hours.

The method shall involve treatment of individuals having mild to medium sleep deprived and cognitive skills and further impacting learning disabilities. The product offers high relaxing and improved quality of life, emotional distress and mood disorders, and cognitive, memory, sleep and performance enhancement.

Referring now to the drawings, and more particularly to FIGS. 1A through 20, where similar reference characters denote corresponding features consistently throughout the figures, there are shown embodiments.

Figure 1B:
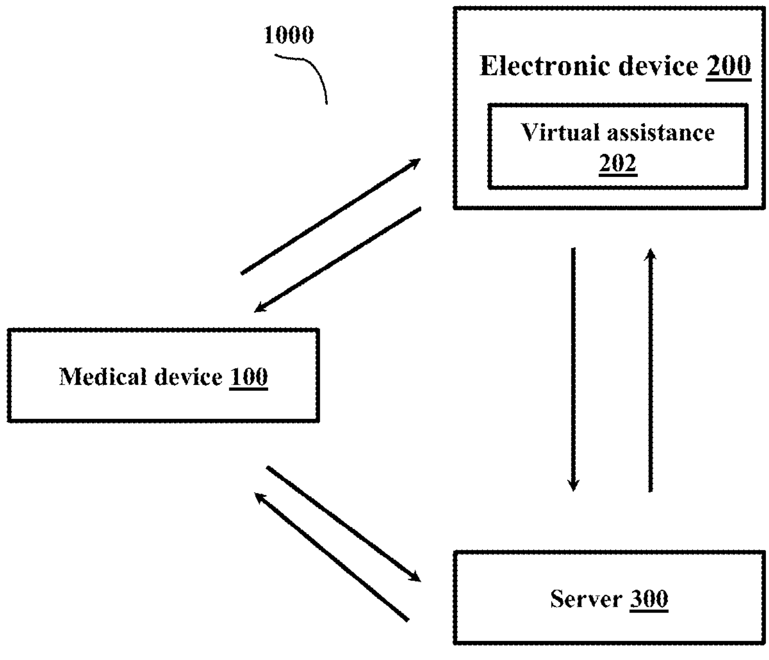

FIG. 1A and FIG. 1B are overviews of a system (1000) for treating a human body part using ultra-low magneto-electric field, according to embodiments as disclosed herein. As shown in the FIG. 1A, the system (1000) includes a medical device (100), an electronic device (200), and a server (300). The medical device (100), the electronic device (200), and the server (300) are communicated with each other using wired communication means and wireless communication means. Also, as shown in the FIG. 1B, the electronic device (200) includes a virtual assistance (202). The medical device (100) can be, for example, but not limited to an electrotherapy device, a wearable band or the like. The electronic device (200) can be, for example, but not limited to a smart phone, a smart watch, a laptop, a desktop, a foldable display or the like. The server (300) can be, for example, but not limited to a cloud server, an edge server, a third party server, or the like. The medical device (100) can be used to support the user need to tackle day-to-day challenges such as work stress, anxiety, restlessness, lack of focus, irregular sleeping patterns and many more problems associated with hyper activated brain.

In an embodiment, the server (300) is configured to acquire one or more amplitude, one or more frequency, one or more phase and one or more rhythm. Based on the one or more acquired amplitude, the one or more acquired frequency, the one or more acquired phase and the one or more acquired rhythm, the server (300) is configured to generate the plurality of ultra-low magneto-electric field. The plurality of ultra-low frequency is in the range of 1 Hz to 900 Hz in 16 bit or 32 bit and 44K to 190 KHz resolution. Further, the server (300) is configured to store the sound file comprises the at least one acquired amplitude, the at least one acquired frequency, the at least one acquired phase and the at least one acquired rhythm. The sound file is stored using wave Algorithms.

Further, the server (300) is configured to convert the plurality of ultra-low magneto-electric field. Further, the server (300) is configured to share the plurality of converted ultra-low magneto-electric field to the electronic device (200).

Further, the electronic device (200) is configured to receive one or more user input, where the one or more user input corresponds to a range of ultra-low magnetic field focused at the back of the neck of the user and also body parts. Based on the one or more user input, the medical device (100) is configured to generate an ultra-low magneto-electric field and modulate (e.g., neuro-modulate or the like) at least one region in the brain, corresponding to the brain activity, monitored using the industry standard EEG brain waves. The electronic device (200) is placed around the neck/cervical neck area/spine. By running programs and generating the magnetic field the user experiences the positive influence of the magnetic field on the brain.

In an embodiment, the brain, corresponding to the brain activity, of the user is modulated by passing a variable electrical signal across the source attached on the media and generating the magnetic field in response to passing the electrical signal across the source attached to the media. The magnetic field modulates activity in the brain where the media is made of magnesium and zinc. The medical device (100) creates the magnetic field, wherein the magnetic field is created in the range of 0.4 to 10 milli gauss. In other words, the frequency from the sound file generates electrical signal, which passes through the copper coil generating the magnetic field, further amplified by the zinc magnesium inductor. The magnetic field has the potential to modulate brain activity.

Further, the server (300) performs various operations (e.g., authenticate the user registration, manage the subscription of the sound files, upload the programs with category, maintain the log of the sound files, maintains log of the programs usage, maintains the electronic device (200) running log for troubleshooting or the like)

The application running in the electronic device (200) performs various operations. The operations can be, for example, but not limited to enable a registration of the user, connecting the electronic device (200) to the medical device (100), downloading a subscribed suit of sound files, syncing the electronic device (200) with the subscribed sound files for at least one of a default program or a subscribed program. A prescribed program for the user based on EEG or any MEG study of Brain Cycles by physician, dashboard for the programs for the user, running the programs for user with specific duration, device running status, battery status, memory status, and copy and update existing programs. The downloading the file from the server (300) through the mobile application to the medical device (100) (e.g., therapeutic device) and update in case of the new program files uploaded/subscribed/prescribed. The programs generate the low magneto electric field which will modulate the brain activity and bring harmony among different parts of the brain areas/regions. In an embodiment, as shown in FIG. 1B, the virtual assistance (202) (e.g., Alexa®, Bixby® or the like) receives an instruction or an input (e.g., voice input, gesture input, or the like) from the user and executes the instruction or the input on the medical device (100) based on the user requirement. Further, the medical device (100) is also used for performing various functions (e.g., taking calls, sending message, streaming media content to the electronic device (200) or the like) in case the electronic device (200) is in an action (e.g., getting normal calls, downloading media content or the like) through a short-range communication module (e.g., Bluetooth module or the like). Also, the electronic device (200) includes a processor (not shown) configured to execute instructions stored in a memory (not shown) and to perform various processes and a communicator (not shown) configured for communicating internally between internal hardware components and with external devices via one or more networks.

In another embodiment, the virtual assistance running in an Internet of things (IoT) environment receives the instruction or the input from the user and executes the instruction or the input on the medical device (100) based on the user requirement.

Figure 2:
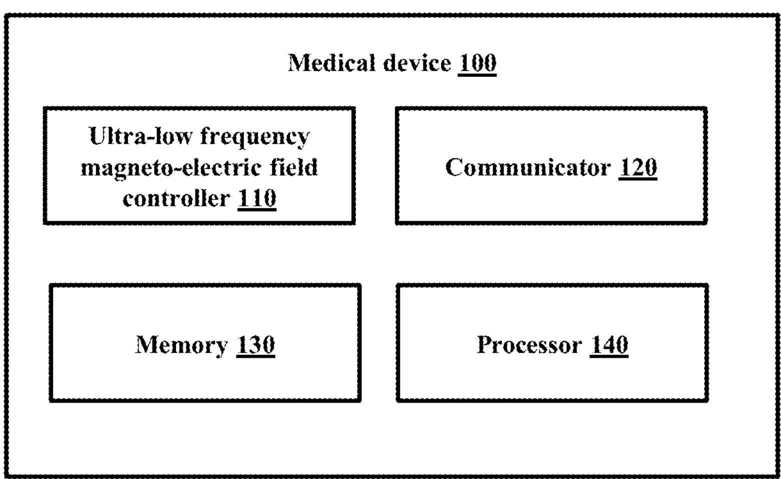
FIG. 2 shows various hardware components of a medical device for treating the human body part using the ultra-low magneto-electric field, according to embodiments as disclosed herein.

FIG. 2 shows various hardware components of the medical device (100) for treating the human body part using the ultra-low magneto-electric field, according to embodiments as disclosed herein. In an embodiment, the medical device (100) includes an ultra-low magneto-electric field controller (110), a communicator (120), a memory (130) and a processor (140). The processor (140) is coupled with the ultra-low magneto-electric field controller (110), the communicator (120) and the memory (130). The ultra-low magneto-electric field controller (110) is configured to acquire the amplitude, the frequency, the phase and the rhythm and generate the plurality of ultra-low magneto-electric field based on the acquired amplitude, the acquired frequency, the acquired phase and the acquired rhythm.

Further, the ultra-low magneto-electric field controller (110) is configured to receive the user input, where the user input corresponds to a range of ultra-low magnetic field focused at a head by placing at the neck of the user. Based on the user input, the ultra-low magneto-electric field controller (110) is configured to generate the ultra-low magneto-electric field from the plurality of ultra-low magneto-electric field by passing the electrical signal across the source attached to the media, and generating the magnetic field in response to passing the electrical signal across the source attached to the media, where the magnetic field harmonizes brain activity. The media is made of a magnesium and zinc.

The medical device (100) belongs to a wearable band with capability to heal the human nervous system pulses. In turn regulates the brain cycles.

Further, the processor (140) is configured to execute instructions stored in the memory (130) and to perform various processes. The communicator (120) is configured for communicating internally between internal hardware components and with external devices via one or more networks. The memory (130) also stores the programs to be executed by the processor (140). The memory (130) can be, for example, but not limited to a Secure Digital (SD) Card or a processor internal memory or any other memory in the medical device (100). The memory (130) may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory (130) may, in some examples, be considered a non-transitory storage medium. The term "non-transitory" may indicate that the storage medium is not embodied in a carrier wave or a propagated signal. However, the term "non-transitory" should not be interpreted that the memory (130) is non-movable. In certain examples, a non-transitory storage medium may store data that can, over time, change (e.g., in Random Access Memory (RAM) or cache).

Further, at least one of the plurality of modules/controller may be implemented through the AI model. A function associated with the AI model may be performed through the non-volatile memory, the volatile memory, and the processor (140). The processor (140) may include one or a plurality of processors. At this time, one or a plurality of processors may be a general purpose processor, such as a central processing unit (CPU), an application processor (AP), or the like, a graphics-only processing unit such as a graphics processing unit (GPU), a visual processing unit (VPU), and/or an AI-dedicated processor such as a neural processing unit (NPU).

The one or a plurality of processors control the processing of the input data in accordance with a predefined operating rule or AI model stored in the non-volatile memory and the volatile memory. The predefined operating rule or artificial intelligence model is provided through training or learning.

Here, being provided through learning means that a predefined operating rule or AI model of a desired characteristic is made by applying a learning algorithm to a plurality of learning data. The learning may be performed in a device itself in which AI according to an embodiment is performed, and/o may be implemented through a separate server/system.

The AI model may comprise of a plurality of neural network layers. Each layer has a plurality of weight values, and performs a layer operation through calculation of a previous layer and an operation of a plurality of weights. Examples of neural networks include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks.

The learning algorithm is a method for training a predetermined target device (for example, a robot) using a plurality of learning data to cause, allow, or control the target device to make a determination or prediction. Examples of learning algorithms include, but are not limited to, supervised learning, unsupervised learning, semi-supervised learning, or reinforcement learning.

Although the FIG. 2 shows various hardware components of the medical device (100) but it is to be understood that other embodiments are not limited thereon. In other embodiments, the medical device (100) may include less or more number of components. Further, the labels or names of the components are used only for illustrative purpose and does not limit the scope of the invention. One or more components can be combined together to perform same or substantially similar function in the medical device (100).

Figure 3A:
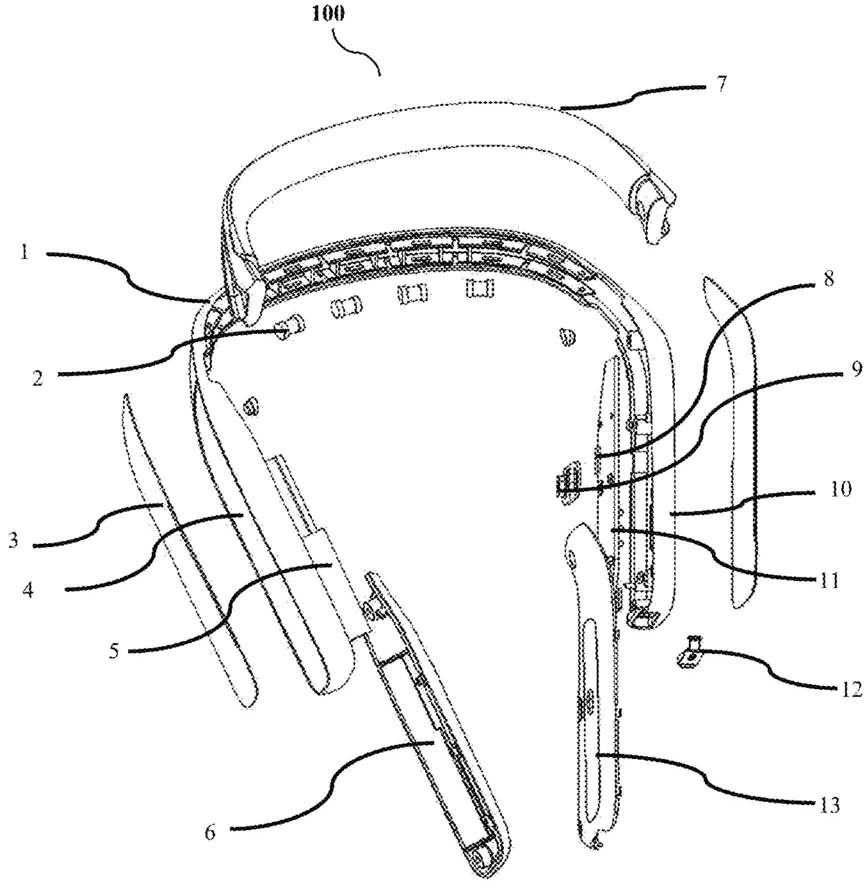
FIG. 3A-FIG. 3C are exploded perspective views of a medical device for treating the human body part using the ultra-low magneto-electric field, according to embodiments as disclosed herein.
Figure 3B:
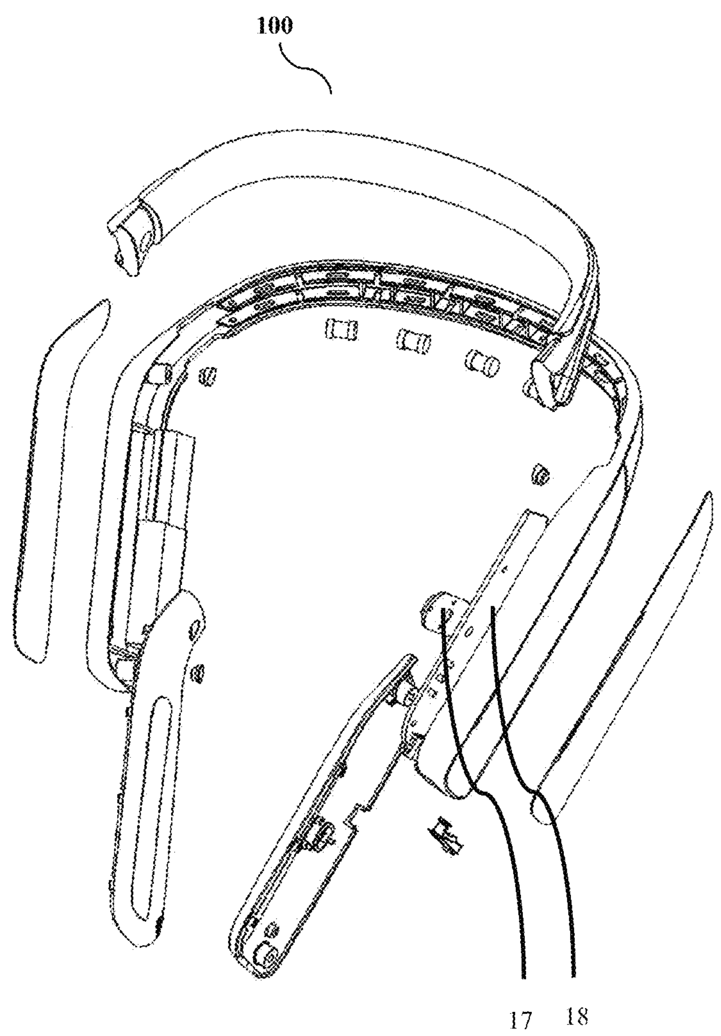
Figure 3C:
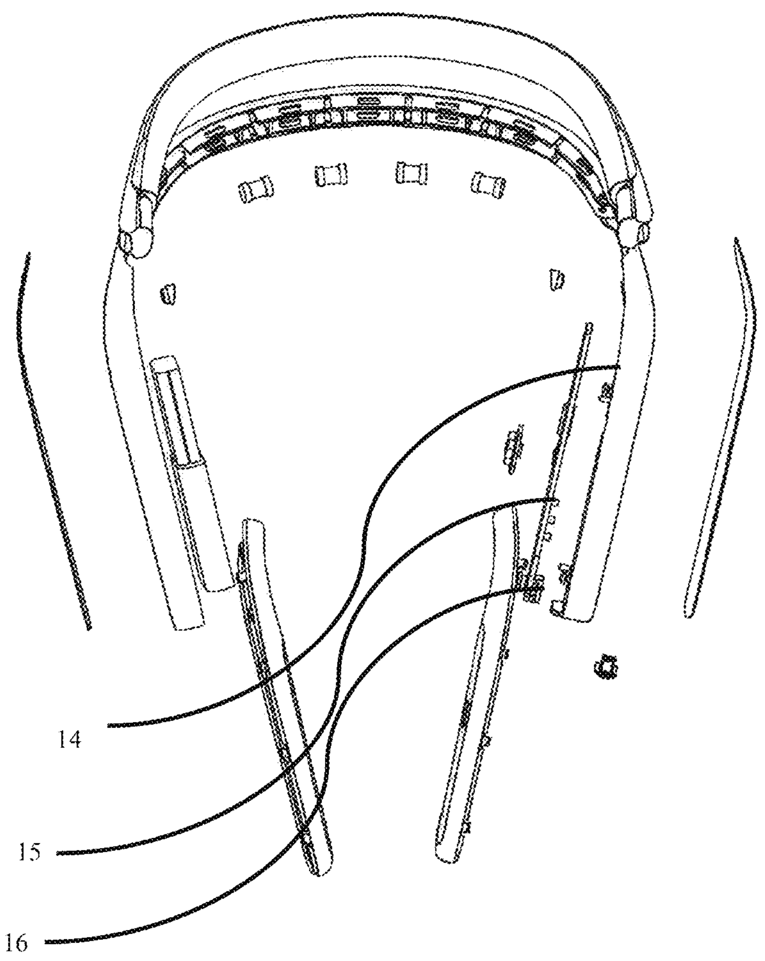

FIG. 3A to FIG. 3C are exploded perspective views of the medical device (100) for treating the human body part using the ultra-low magneto-electric field, according to embodiments as disclosed herein. The functions and operations of the medical device (100) is already explained in connection with the FIG. 2. Further, the medical device (100) also includes a media holder top (1), an media (2), a side panel sticker (3), a battery holder top (4), a battery (5), a battery holder bottom (6), an media holder bottom (7), a power ON/OFF (8), a button (9), a PCB holder top (10), a LED (11), a USB cover (12), a PCB holder bottom (13), a PCB holder (14), a Bluetooth (15), a USB connector (16), buttons (17) and a Wireless module (18). The media (2) is arranged between the media holder top (1) and the media holder bottom (7). The battery (5) is arranged between the battery holder top (4) and the battery holder bottom (6). A switch is used for ON/OFF the medical device (100). A reset switch is used for Bluetooth (BT) waking up the medical device (100). A USB port is used for charging and a light indicator is used for indicting a charging, low battery condition, a full battery condition, and program running in the electronic device (200) and BT active state.

Figure 3D:
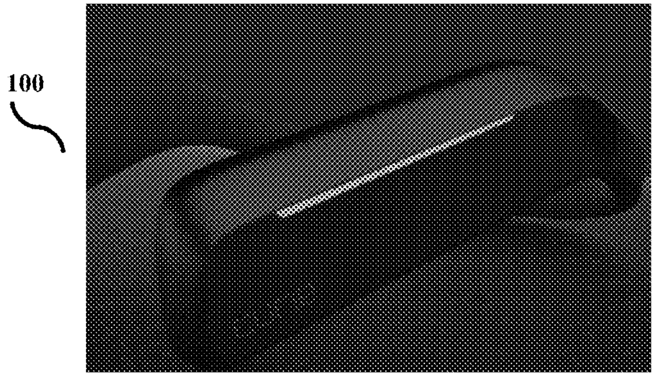
FIG. 3D-FIG. 3F are example perspective views of a medical device for treating the human body part using the ultra-low magneto-electric field, according to embodiments as disclosed herein.
Figure 3E:
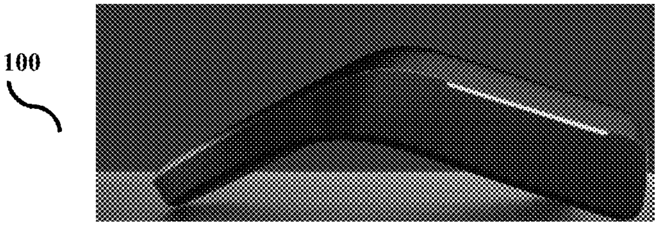
Figure 3F:
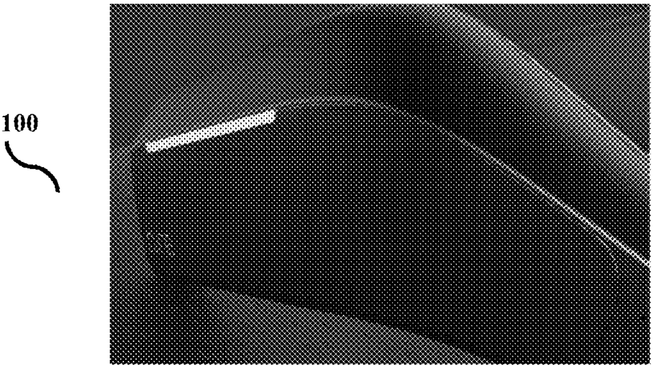

FIG. 3D-FIG. 3F are example perspective views of the medical device (100) for treating the human body part using the ultra-low magneto-electric field, according to embodiments as disclosed herein.

Figure 4:
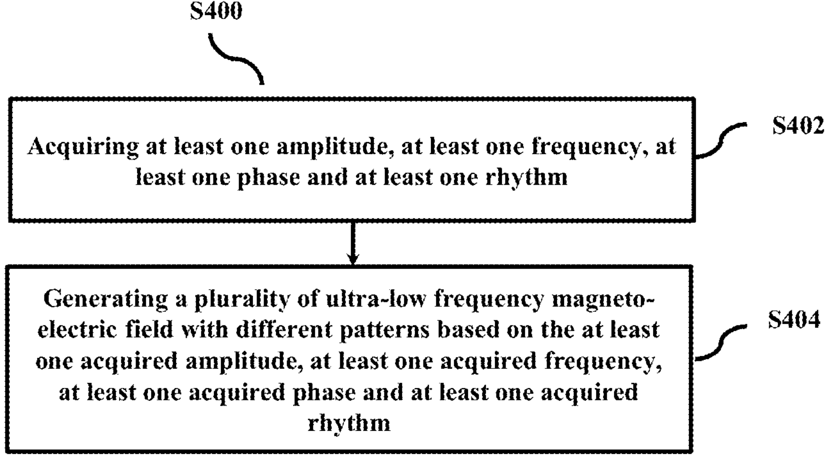
FIG. 4 is a flow chart illustrating a method for treating the human body part using ultra-low magneto-electric field, according to embodiments as disclosed herein.

FIG. 4 is a flow chart (S400) illustrating a method, implemented by the server (300) and/or the medical device (100) for treating the human body part using the ultra-low magneto-electric field, according to embodiments as disclosed herein. At S402, the method includes acquiring the one or more amplitude, the one or more frequency, the one or more phase and the one or more rhythm. At S404, the method includes generating the plurality of ultra-low magneto-electric field based on the one or more acquired amplitude, the one or more acquired frequency, the one or more acquired phase and the one or more acquired rhythm.

Figure 5:
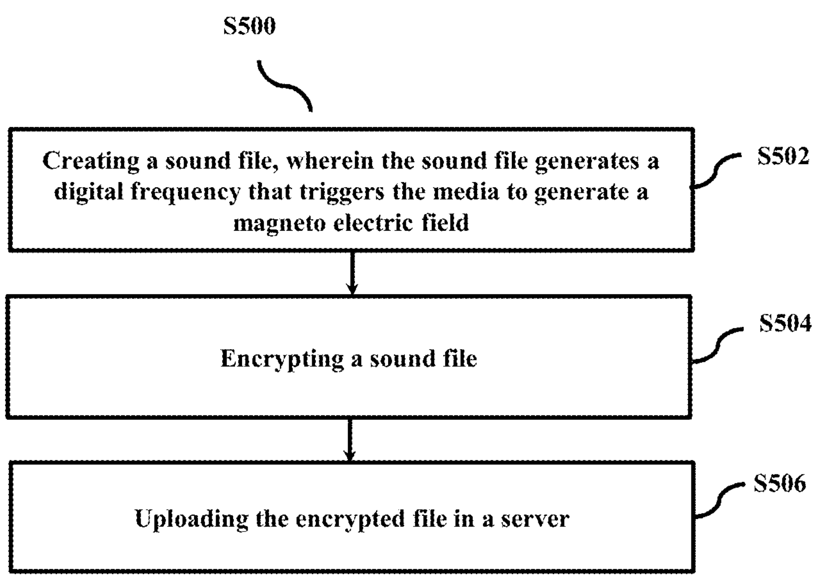
FIG. 5 is another flow chart illustrating a method for treating the human body part using ultra-low magneto-electric field, according to embodiments as disclosed herein.

FIG. 5 is another flow chart (500) illustrating a method for treating the human body part using ultra-low magneto-electric field, according to embodiments as disclosed herein. At S502, the method includes creating the sound file. The sound file generates the frequency that triggers the media (2) (e.g., ferromagnetic inductor or the like) to generate the magneto electric field (MEF). At S504, the method includes encrypting the sound file. At S506, the method includes uploading the encrypted file in the server (300).

Figure 6:
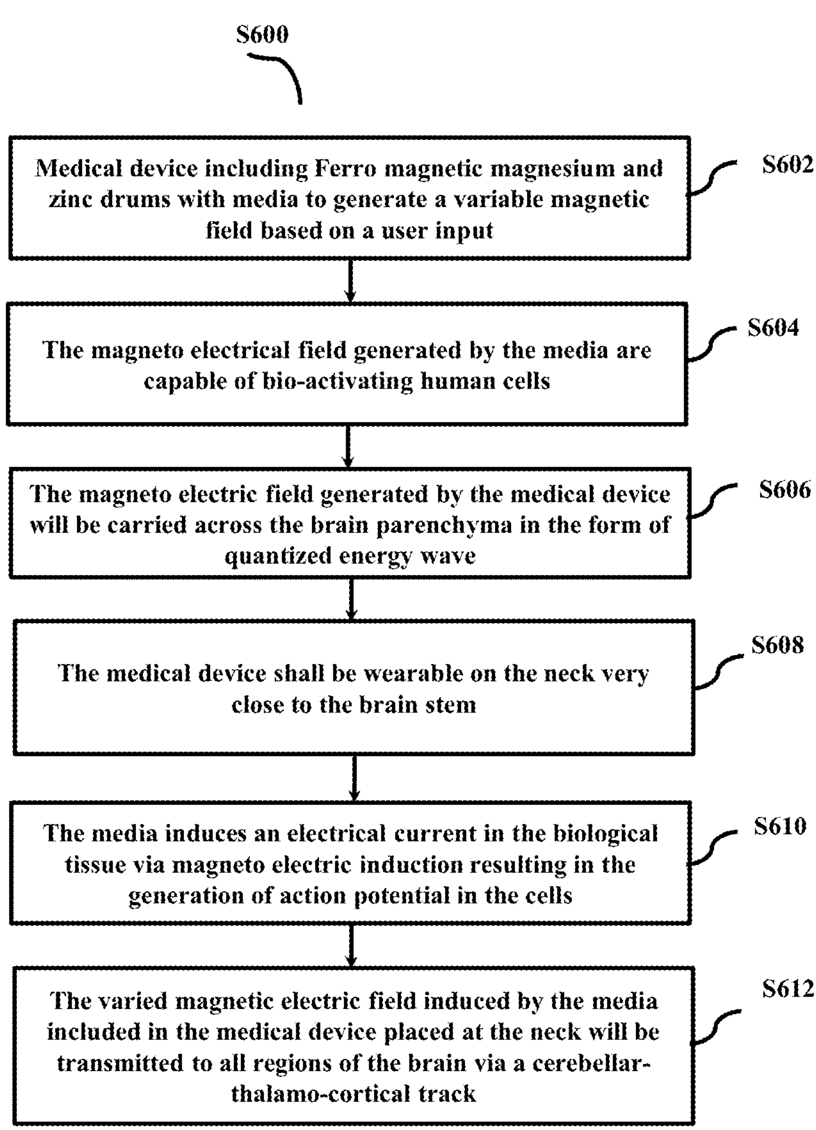
FIG. 6 is a flow chart illustrating a method, implemented by the medical device, for treating the human body part using the ultra-low magneto-electric field, according to embodiments as disclosed herein.

FIG. 6 is a flow chart (600) illustrating a method, implemented by the medical device (100), for treating the human body part using the ultra-low magneto-electric field, according to embodiments as disclosed herein. At S602, the medical device (100) including the Ferro magnetic magnesium and zinc drums with ferromagnetic inductor to generate the variable magnetic field based on the user input. At S604, the magneto electrical signals generated by the media (2) (e.g., ferromagnetic inductor) are capable of modulating the brain activity. At S606, the magnetic electric signals generated by the medical device (100) will be carried across the brain in the form of quantized energy waves. The magneto-electric signal is a signal with specific frequency, phase, amplitude and rhythm. At S608, the medical device (100) shall be wearable on the back of the neck very close to the cervical spine. At S610, the media (2) (e.g., ferromagnetic inductor or the like) induces an electrical current in the biological tissue via magnetic electric induction resulting in the generation of action potential in the cells. At S612, the varied magnetic electric signals induced by the media (2) (e.g., ferromagnetic inductor) included in the medical device (100) placed at the neck will be transmitted to all regions of the brain via a cerebellar-thalamo-cortical track.

Figure 7:
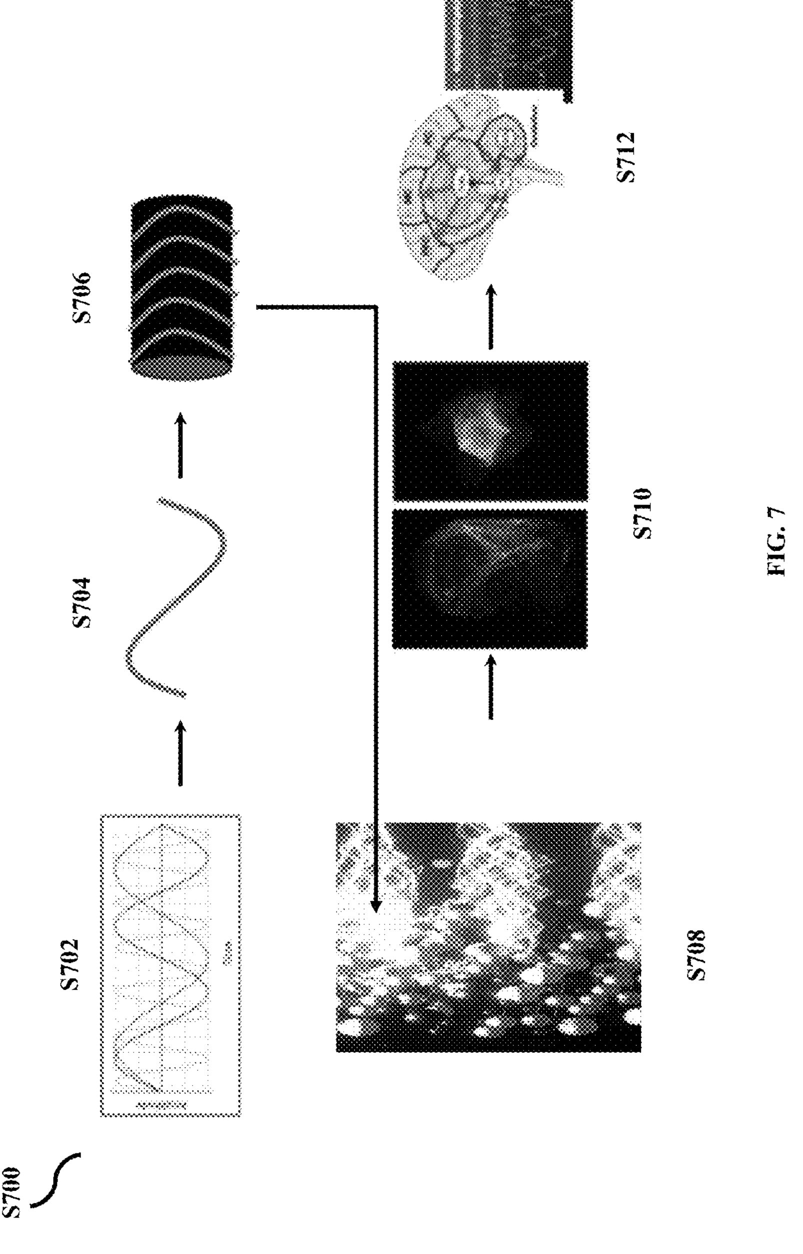
FIG. 7 is an example illustration in which a human body part treatment is depicted using the ultra-low magneto-electric field, according to embodiments as disclosed herein.

FIG. 7 is an example illustration in which a human body part treatment is depicted using the ultra-low magneto-electric field, according to embodiments as disclosed herein. At S702, the sound files are generated and stored as long variable frequency. The long variable frequency is stored in own encrypted audio format. At S704, the long variable frequency in digital form carry milli-volts electricity. At S706, the electrical signals hit the media (2). At S708, the magnetic field is generated through the media (2). At S710, the transmitted long wavelength energy waves in the media (2) generates the variable magnetic field within the range of 0.4 to 10 milli Gauss. At S712, the generated magnetic field harmonizes brain activity.

Figure 8:
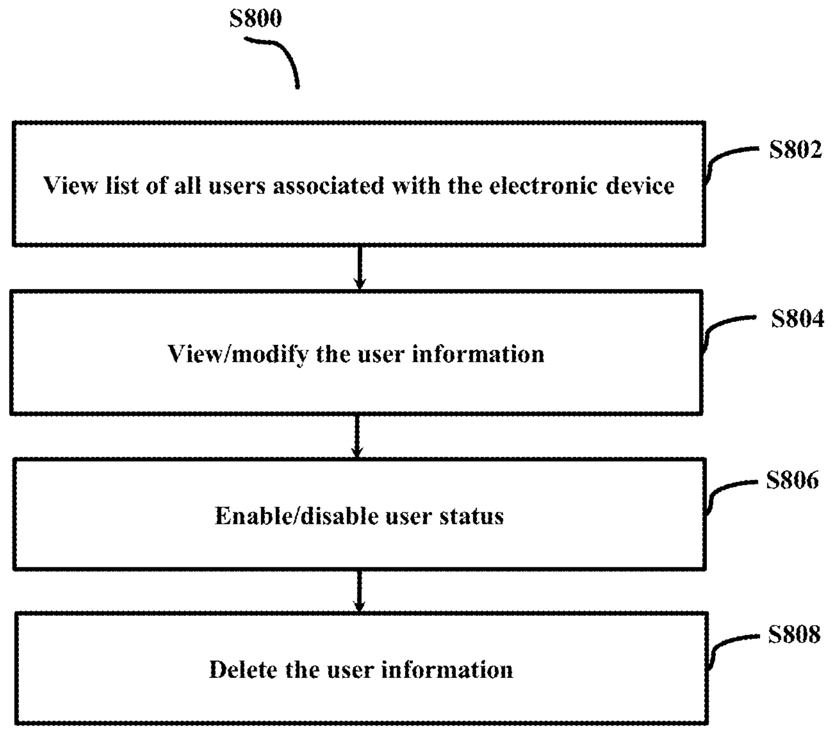
FIG. 8 is an example flow chart illustrating a user management, according to embodiments as disclosed herein.

FIG. 8 is an example flow chart (S800) illustrating a user management, according to embodiments as disclosed herein. S802, the server (300) views the list of all users associated with the electronic device (200). At S804, the server (300) views/modifies the user information. At S806, the server (300) enables/disables the user status. At S808, the server (300) deletes the user information. In the proposed method, the goal setting hours are suggested to the user then the user provides the input for suggested hours of programs running.

Figure 9:
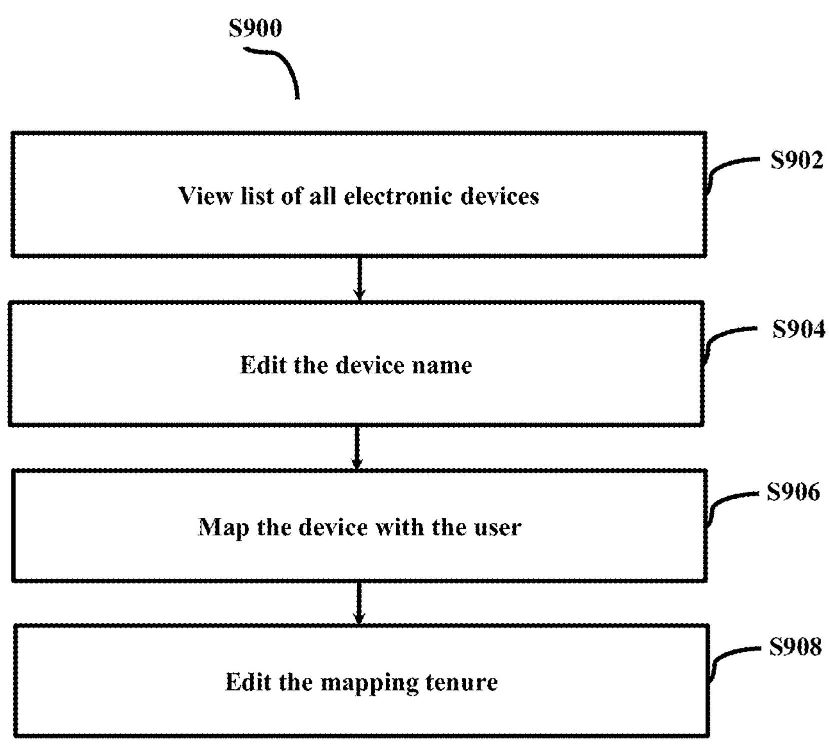
FIG. 9 is an example flow chart illustrating a device management, according to embodiments as disclosed herein.

FIG. 9 is an example flow chart (S900) illustrating a device management, according to embodiments as disclosed herein. At S902, the server (300) views the list of all electronic devices (200). At S904, the server (300) edits the device name. At S906, the server (300) maps the device (200) with the user. At S908, the server (300) edits the mapping tenure.

Figure 10:
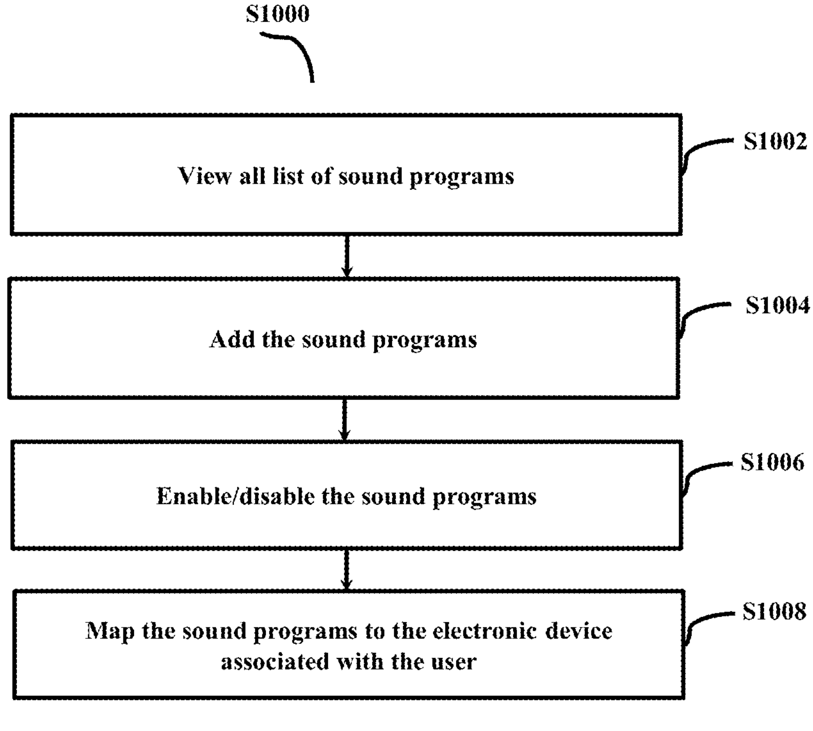
FIG. 10 is an example flow chart illustrating a program management, according to embodiments as disclosed herein.

FIG. 10 is an example flow chart (S1000) illustrating a program management, according to embodiments as disclosed herein. At S1002, the method includes viewing all list of sound programs. At S1004, the method includes adding the sound programs. At S1006, the method includes enabling/disabling the sound programs. At S1004, the method includes mapping the sound programs to the electronic device (200) associated with the user.

Figure 11:
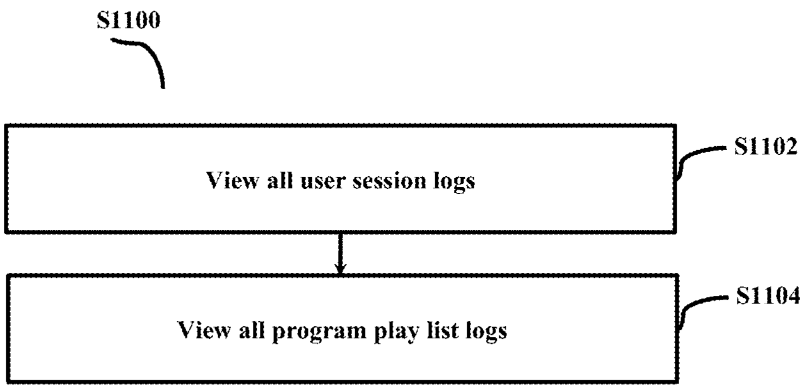
FIG. 11 is an example flow chart illustrating a log management, according to embodiments as disclosed herein.

FIG. 11 is an example flow chart (S1100) illustrating a log management, according to embodiments as disclosed herein. At S1102, the method includes viewing all user session logs. At S1104, the method includes viewing all program play list logs.

Figure 12:
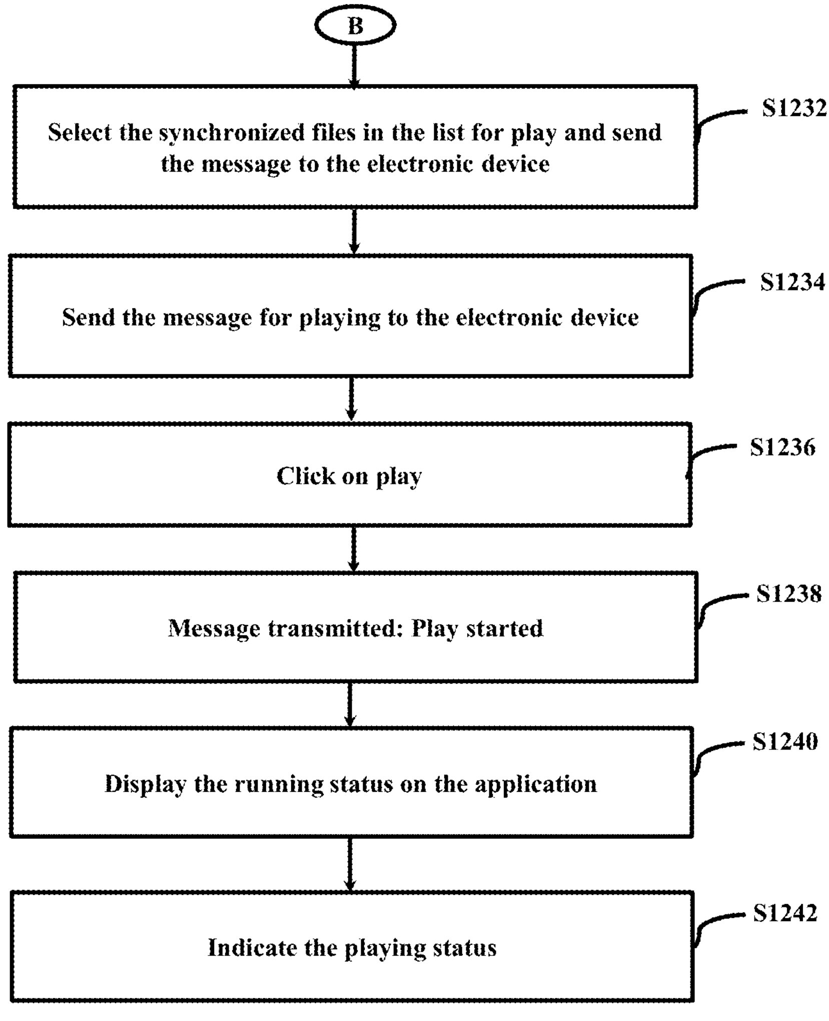
FIG. 12 is an example flow chart illustrating various operations for treating the human body part using the ultra-low magneto-electric field, according to embodiments as disclosed herein.
Figure 12:
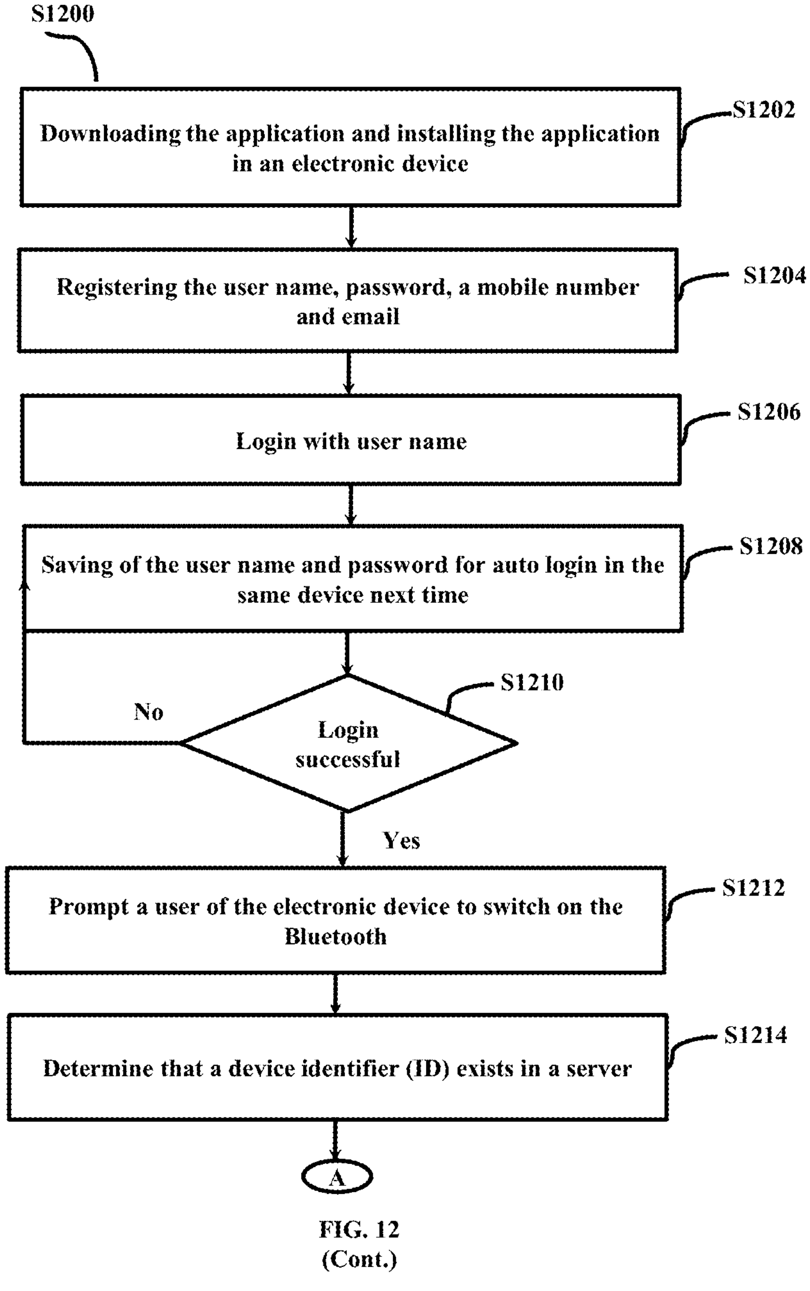
Figure 12:
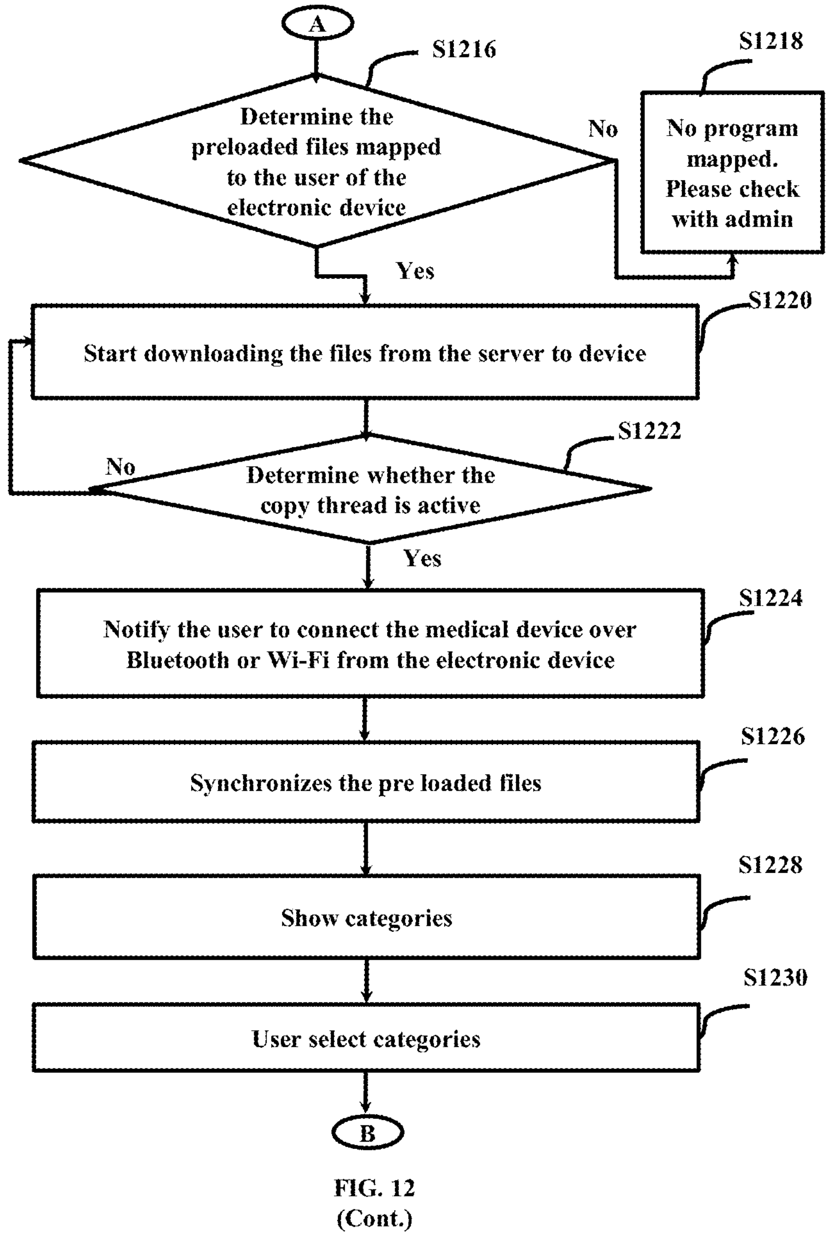

FIG. 12 is an example flow chart (S1200) illustrating various operations for treating the human body part using the ultra-low magneto-electric field, according to embodiments as disclosed herein.

At S1202, the method includes downloading the application and installing the application in the electronic device (200). At S1204, the method includes registering the user name, a password, a mobile number and an email with the application. At S1206, the method includes performing the login with the user name. At S1208, the method includes saving of the user name and password for auto login in the same device for the next time. At S1210, the method includes determining whether the login is successful. If the login is successful then, at S1212, the method includes prompting the user of the electronic device (200) to switch on the Bluetooth. If the login is not successful then, the method performs the step S1208 again. At S1214, the method includes determining that a device identifier (ID) exists in the server (300).

At S1216, the method includes determining whether the preloaded files mapped to the user of the electronic device (200). If the preloaded files are mapped to the user of the electronic device (200) then, at S1220, the method includes starting downloading the files from the server (300) to the medical device (100). If the preloaded files are not mapped to the user of the electronic device (200) then, at S1218, the method includes notifying an action (e.g., no program mapped and please check with admin).

At S1222, the method includes determining whether the copy thread is an active. If the copy thread is not an active then, the method performs the steps of S1220. At S1224, the method includes notifying the user to connect the medical device (100) over the Bluetooth or the Wi-Fi from the electronic device (200).

At S1226, the method includes synchronizing the preloaded files. At S1228, the method includes showing the categories. At S1230, the method allows that the user selects the categories. At S1232, the method includes selecting the synchronized files in the list for play and repeating the mode and sending the message to the electronic device (200). At S1234, the method includes sending the message for playing to the electronic device (200). At S1236, the method includes clicking on play. At S1238, the method allows that the message transmitted: Play started. At S1240, the method includes displaying the running status on the application. At S1242, the method includes indicating the playing status.

Figure 13:
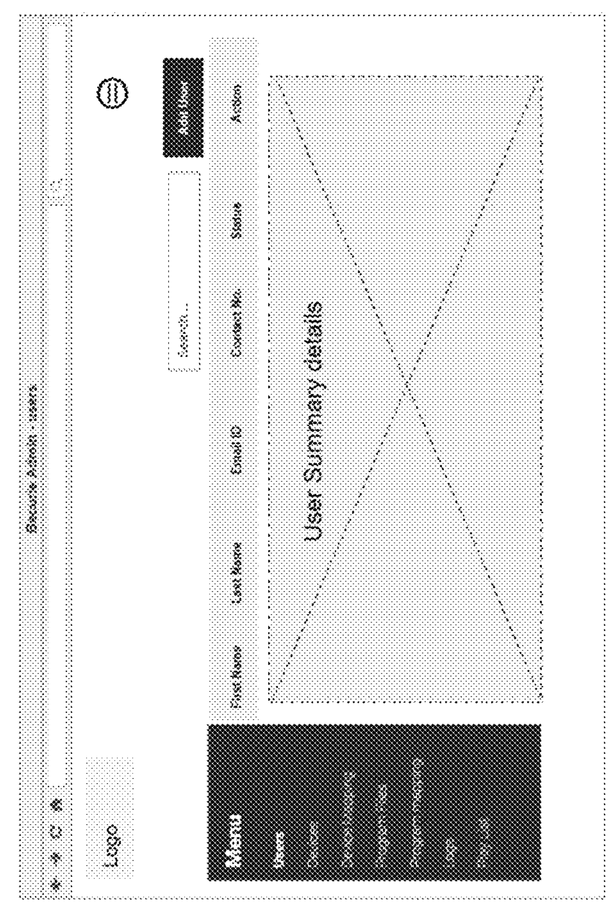
FIG. 13 is an example illustration in which user summary details are depicted, according to embodiments as disclosed herein.

FIG. 13 is an example illustration (S1300) in which user summary details are depicted, according to embodiments as disclosed herein. As shown in the FIG. 13, a user view illustrating the user interface (UI) of the server (300) consist of the list of all users registered through the electronic device (200). The method can be used to activate/in-activates the user from an administrator account and also the method can be used to view all the information related to the user.

Figure 14:
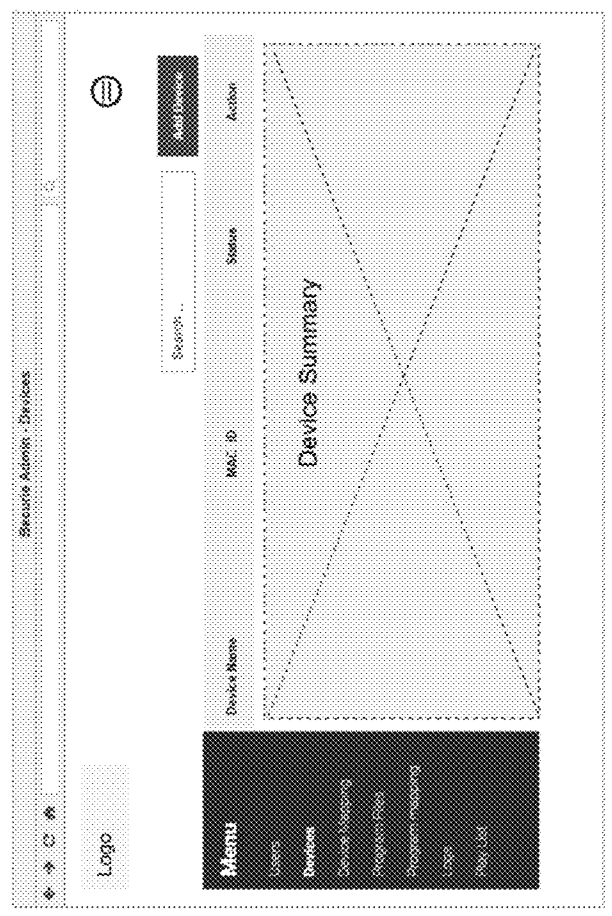
FIG. 14 is an example illustration in which device summary details are depicted, according to embodiments as disclosed herein.

FIG. 14 is an example illustration (S1400) in which device summary details are depicted, according to embodiments as disclosed herein. A device wireframe illustrates a user interface (UI) of the server (300) which consists of list of all devices which are mapped to a specific user account through electronic device (200).

Figure 15:
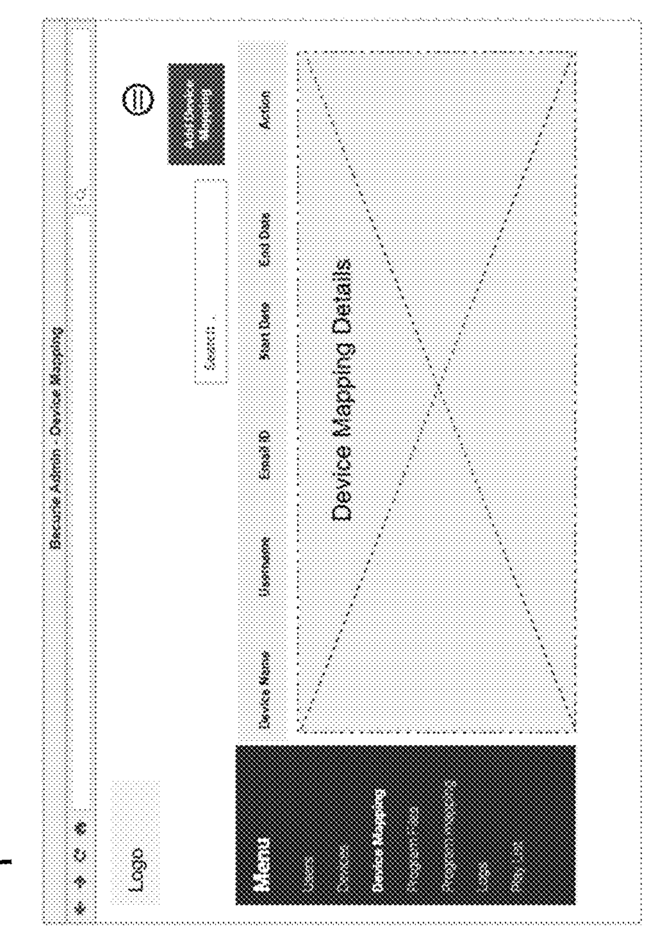
FIG. 15 is an example illustration in which device mapping details are depicted, according to embodiments as disclosed herein.

FIG. 15 is an example illustration (S1500) in which device mapping details are depicted, according to embodiments as disclosed herein. As shown in the FIG. 15, a device mapping wireframe illustrates a user interface (UI) of the server (300) in which programs shall be mapped and unmapped to a specific user. The method can be used to update the validity dates against the user and to the specific electronic device.

Figure 16:
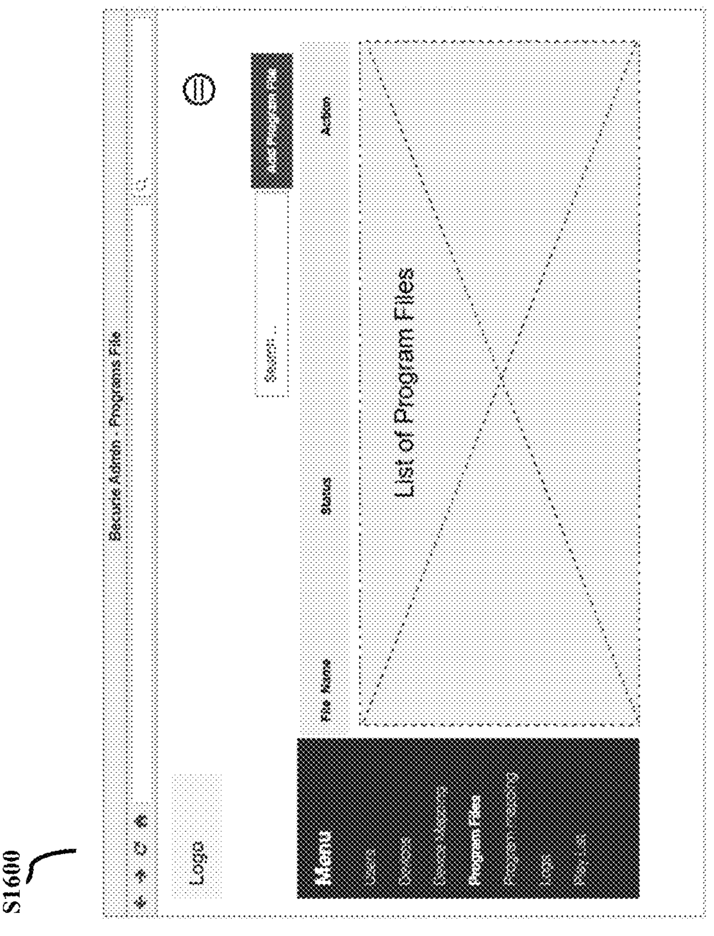
FIG. 16 is an example illustration in which list of program files details are depicted, according to embodiments as disclosed herein.

FIG. 16 is an example illustration (S1600) in which list of program files details are depicted, according to embodiments as disclosed herein. As shown in the FIG. 16, a program files wireframe illustrates a user interface (UI) of the server (300) in which a list of all programs that are available at the server (300) along with their status i.e., active state or inactive state. The method has provision to a dd a new program file externally and delete the program permanently from the server (300).

Figure 17:
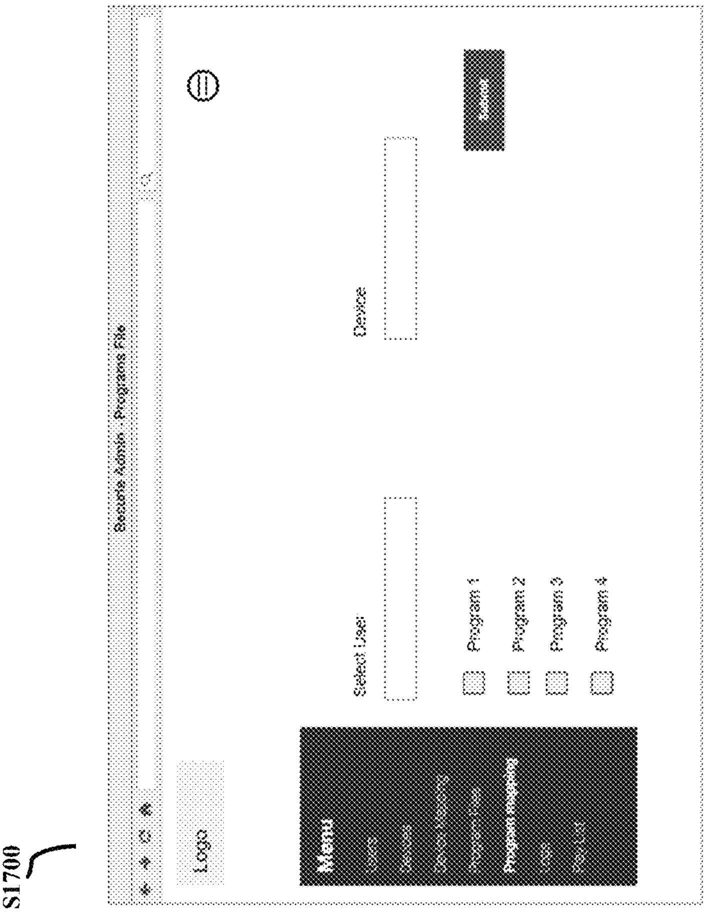
FIG. 17 is an example illustration in which program mapping details are depicted, according to embodiments as disclosed herein.

FIG. 17 is an example illustration (S1700) in which program mapping details are depicted, according to embodiments as disclosed herein. As shown in the FIG. 17, a program mapping wireframe illustrates a user interface (UI) of the server (300) in which the method can be used to map a new program file to a specific user or un-map the existing program file from the specific user.

Figure 18:
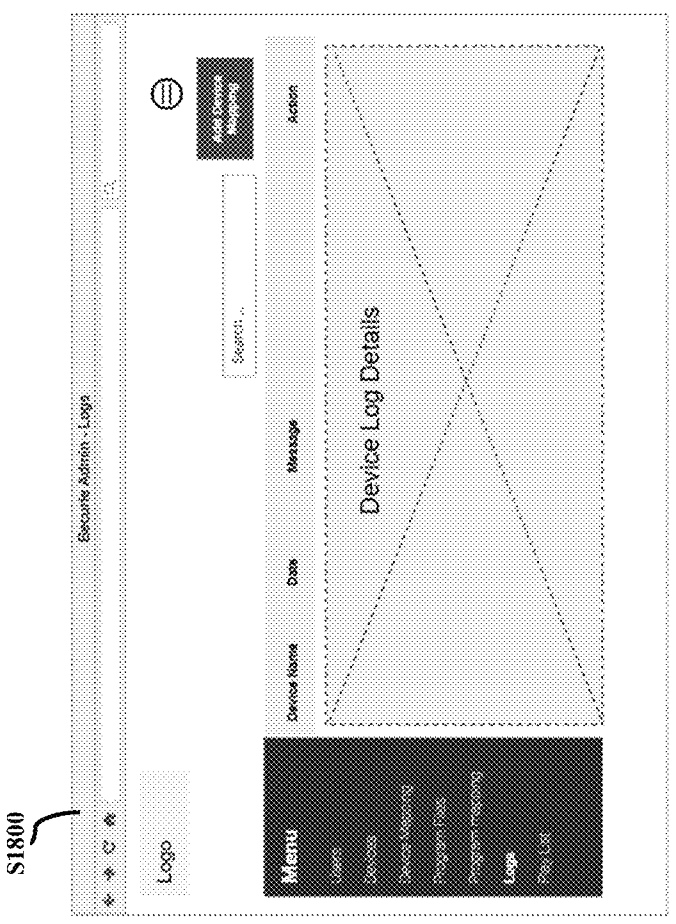
FIG. 18 is an example illustration in which device logs details are depicted, according to embodiments as disclosed herein.

FIG. 18 is an example illustration (S1800) in which device logs details are depicted, according to embodiments as disclosed herein. As shown in the FIG. 18, a device log" wireframe illustrates a user interface (UI) of the server (300) in which the method can be used to show the historical data of communication happened/protocols triggered between the electronic device (200) and the medical device (100).

Figure 19:
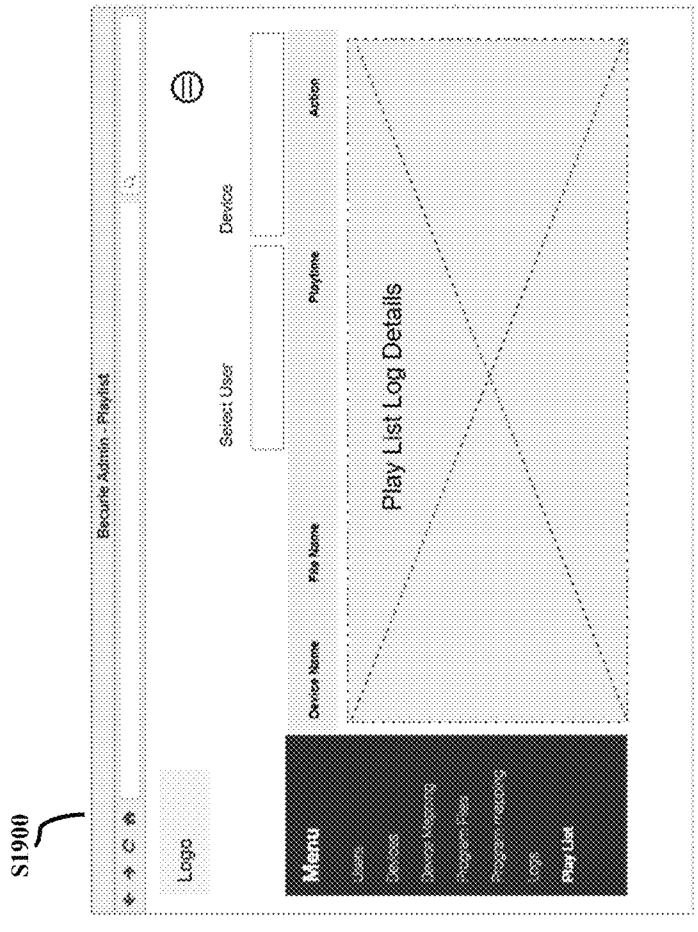
FIG. 19 is an example illustration in which play list logs details are depicted, according to embodiments as disclosed herein.

FIG. 19 is an example illustration (S1900) in which play list logs details are depicted, according to embodiments as disclosed herein. As shown in the FIG. 19, a program mapping wireframe (illustrates a UI of the server (300) in which the method can be used to show the user specific program files history recorded between the electronic device (200) and the medical device (100).

Figure 20:
FIG. 20 is an example illustration in which device functional flow is depicted, according to embodiments as disclosed herein.
Figure 20:
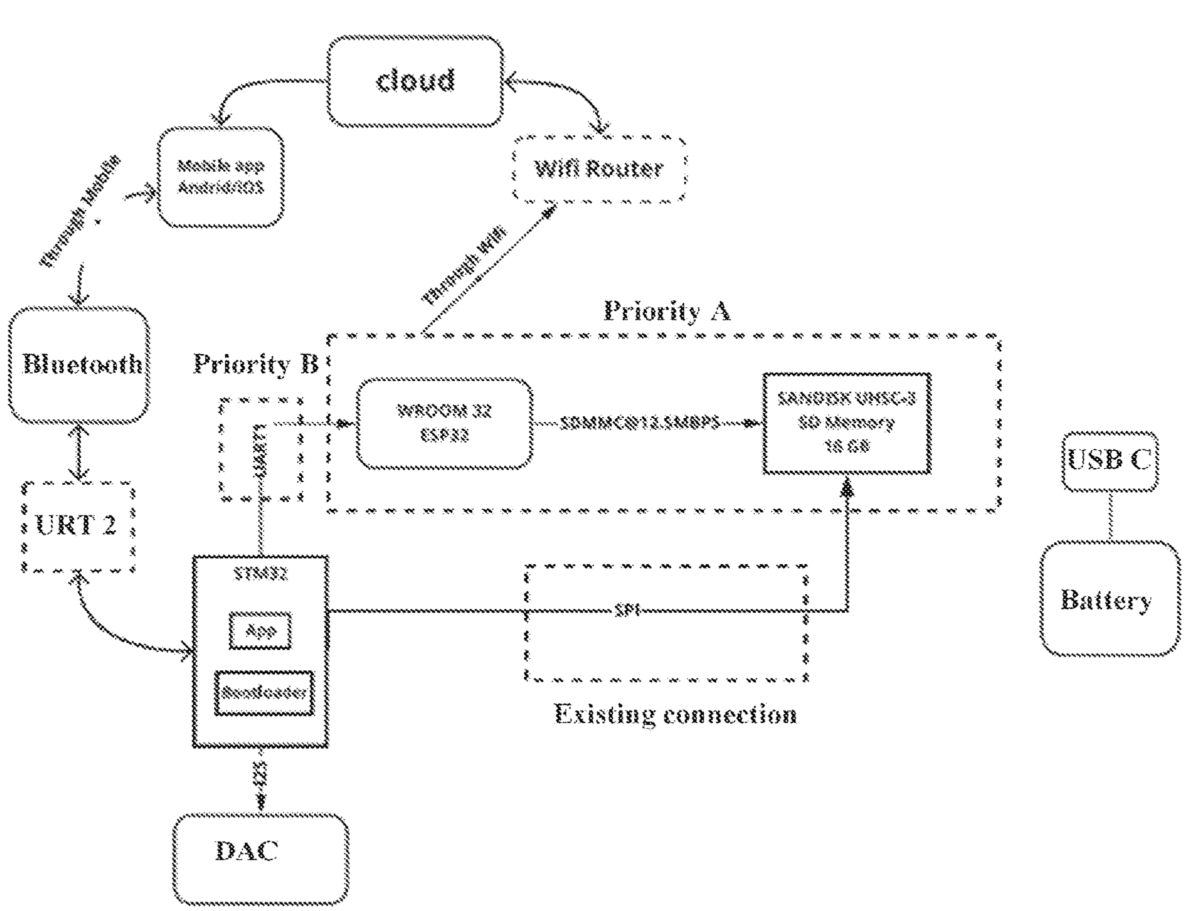

FIG. 20 is an example illustration (S2000) in which device functional flow is depicted, according to embodiments as disclosed herein. As shown in the FIG. 20, an internal hardware architecture of the medical device (100) illustrates file transfer mechanism among the server (300), the medical device (100) and the electronics device (200). The FIG. 20 is explained in connection with the FIG. 12. At S2000, the method includes determining whether the copy thread is an active. If the copy thread is not an active then, the method performs the steps of S1220. At S1224, the method includes notifying the user to connect the medical device (100) over the Bluetooth or the Wi-Fi from the electronic device (200).

The various actions, acts, blocks, steps, or the like in the flow charts (S400-S1200) may be performed in the order presented, in a different order or simultaneously. Further, in some embodiments, some of the actions, acts, blocks, steps, or the like may be omitted, added, modified, skipped, or the like without departing from the scope of the invention.

The goal Monitoring, the program running status, device running status for any kind of issues in the electronic device (200) is clarified using the queries on the device function. The program running status update on the application with update coming from the electronic device (200) on the program running.

In the proposed method, the one user can use multiple devices and the one device is used by multiple user.

Please note that the various schematic diagrams (e.g., internal hardware architecture of the medical device (100) or the like) are provided example illustrative purpose. Further, it could possible to implement various schematic diagrams, based on the requirement and need of the invention, within the scope of the invention.

The embodiments disclosed herein can be implemented through at least one software program running on at least one hardware device and performing network management functions to control the network elements.

Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in at least one embodiment through or together with a software program written in e.g., Very high-speed integrated circuit Hardware Description Language (VHDL) another programming language, or implemented by one or more VHDL or several software modules being executed on at least one hardware device. The hardware device can be any kind of portable device that can be programmed. The device may also include means which could be e.g., hardware means like e.g., an ASIC, or a combination of hardware and software means, e.g., an ASIC and an FPGA, or at least one microprocessor and at least one memory with software modules located therein. The method embodiments described herein could be implemented partly in hardware and partly in software. Alternatively, the invention may be implemented on different hardware devices, e.g., using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments and examples, those skilled in the art will recognize that the embodiments and examples disclosed herein can be practiced with modification within the spirit and scope of the embodiments as described herein.

I claim:

1. A method for treating a human body part using ultra-low magneto-electric field, the method comprising:

generating, by a server (300), one or more program files comprising at least one amplitude, at least one frequency, at least one phase and at least one rhythm;

downloading, by an electronic device (200), the one or more program files from the server (300) and sharing the one or more program files with a medical device (100);

receiving, by the electronic device (200), one or more user input corresponding to a range of ultra-low magnetic-electric fields focused at a head or a neck of a user;

generating, by the medical device (100), a plurality of ultra-low magneto-electric fields based on the one or more program files;

based on the user input, generating, by the medical device (100), the ultra-low magneto-electric fields from the plurality of ultra-low magneto-electric fields by passing an electrical signal across a source attached to a media (2), wherein the media (2) is made of magnesium and zinc and the source is made of copper, and generating a magnetic field in response to passing the electrical signal across the source attached to the media (2), wherein the magnetic field is created in the range of 0.4 to 10 milli gauss; and modulating brain activity based on the generated magnetic field, wherein the brain activity is monitored using an industry standard electroencephalogram (EEG).

2. The method as claimed in claim 1, wherein the method comprises:

storing, by the server (300) the one or more program files comprising the at least one acquired amplitude, the at least one acquired frequency, the at least one acquired phase and the at least one acquired rhythm; and allowing a user of at least one of the electronic device (200) and the medical device (100) to download the one or more program files to the medical device through the electronic device (200).

3. The method as claimed in claim 1, wherein the one or more program files are generated and stored as long variable frequency, and wherein the long variable frequency is stored in an encrypted audio format.

4. The method as claimed in claim 1, wherein the plurality of ultra-low magneto-electric fields is in the range of 1 Hz to 900 Hz in 16 bit or 32 bit and 44 KHz to 190 KHz resolution.

5. The method as claimed in claim 1, wherein the medical device (100) comprises:

a media holder top (1), a media holder bottom (7), a media (2), wherein the media (2) is placed between the media holder top (1) and the media holder bottom (7), a side panel ticker (3), a battery holder top (4), a battery holder bottom (6), a battery (5), wherein the battery (5) is placed between the battery holder top (4) and the battery holder bottom (6), a LED (11), a short-range communication module configured to communicate with the electronic device, a USB connector (16), wherein the USB connector (16) is configured to charge the medical device, a button (17), a reset switch for the short-range communication module to wake up the medical device (100); and a light indicator (11) used for indicating a charging condition, a low battery condition, a full battery condition, a program file running indication in the medical device (100) and an active state of the short-range communication module.

6. The method as claimed in claim 1, wherein the one or more program files comprises the at least one acquired amplitude, the at least one acquired frequency, the at least one acquired phase, and the at least one acquired rhythm is stored in the server, wherein the server is configured to perform one or more actions comprising authenticating a user registration, managing a subscription of the one or more program files, uploading the one or more program files with category, maintaining a log of the one or more program files, maintaining log of a program file usage, and maintaining the electronic device (200) running log for troubleshooting.

7. The method as claimed in claim 1, wherein an application running in the electronic device (200) performs at least one operation comprising:

enabling a registration of a user;

connecting the electronic device (200) to the medical device (100);

enable downloading a subscribed set of program files;

syncing the medical device (100) with the subscribed set of program files for at least one of a default program, a subscribed program, and a prescribed program for the user; and displaying at least one of a program file dashboard, device running status, battery status, memory status, and allowing copying or updating existing program files.

8. The method as claimed in claim 1, wherein a virtual assistant running in at least one of an Internet of things (IoT) environment or the electronic device (200) is configured to receive an input from a user of the at least one medical device (100) and the electronic device (200) and execute the input on the medical device (100) based on the user requirement.

9. A system (1000) for treating a human body part using ultra-low magneto-electric fields, the system (1000) comprising:

a medical device (100);

an electronic device (200); and a server (300), wherein the server (300) is configured to:

generate one or more program files comprising at least one amplitude, at least one frequency, at least one phase and at least one rhythm;

wherein the electronic device (200) is configured to:

download the one or more program files from the server (300) and share the one or more program files with a medical device (100); and receive one or more user input corresponding to a range of ultra-low magneto-electric fields configured to be focused at a head or a neck of a user;

and wherein the medical device (100) is configured to:

generate a plurality of ultra-low magneto-electric fields based on the one or more program files; and based on the user input, generate, by the medical device (100), the ultra-low magneto-electric field from the plurality of ultra-low magneto-electric fields by passing an electrical signal across a source attached to a media (2), wherein the media (2) is made of magnesium and zinc and the source is made of copper, and generate a magnetic field in response to passing the electrical signal across the source attached to the media (2), wherein the magnetic field is created in the range of 0.4 to 10 milli gauss; and modulate brain activity based on the generated magnetic field, wherein the brain activity is monitored using an industry standard electroencephalogram (EEG).

10. The system (1000) as claimed in claim 9, wherein the one or more program files are generated and stored as long variable frequency, and wherein the long variable frequency is stored in an encrypted audio.

11. The system (1000) as claimed in claim 9, wherein the plurality of ultra-low magneto-electric fields is in the range of 1 Hz to 900 Hz in 16 bit or 32 bit and 44 KHz to 190 KHz resolution.

12. The system (1000) as claimed in claim 9, wherein the medical device (100) comprises:

a media holder top (1), a media holder bottom (7), a media (2), wherein the media (2) is placed between the media holder top (1) and the media holder bottom (7), a side panel ticker (3), a battery holder top (4), a battery holder bottom (6), a battery (5), wherein the battery (5) is placed between the battery holder top (4) and the battery holder bottom (6), a LED (11), a short-range communication module configured to communicate with the electronic device, a USB connector (16), wherein the USB connector (16) is configured to charge the medical device, a button (17), a reset switch for the short-range communication module to wake up the medical device (100); and a light indicator used for indicating a charging condition, a low battery condition, a full battery condition, a program file running in the medical device (100) and an active state of the short-range communication module.

13. The system (1000) as claimed in claim 9, wherein the server (300) is configured to perform one or more actions comprising authenticating a user registration, managing a subscription of one or more program files, uploading the one or more program files with category, maintaining a log of the one or more program files, maintaining log of a program file usage, and maintaining the electronic device (200) running log for troubleshooting.

14. The system (1000) as claimed in claim 9, wherein an application running in the electronic device (200) performs at least one operation comprising:

enabling a registration of a user;

connecting the electronic device (200) to the medical device (100);

downloading a subscribed set of program files;

syncing the electronic device (200) with the subscribed set of program files;

displaying at least one of a program file dashboard device running status, battery status, memory status, and allowing copying and updating existing program files.

15. A medical device (100) for treating a human body part using ultra-low magneto-electric fields, the medical device (100) comprising:

a processor (140);

a memory (130); and an ultra-low magneto-electric field controller (110), coupled with the processor (140) and the memory (130), is configured to:

receive at least one program file comprising at least one amplitude, at least one frequency, at least one phase and at least one rhythm;

generate, based on the received at least one program file and a user input corresponding to a range of ultra-low magnetic field focused at a head or a neck of a user, an ultra-low magneto-electric field from a plurality of ultra-low magneto-electric fields by passing an electrical signal across a source attached to a media (2), wherein the media (2) is made of magnesium and zinc and the source is made of copper, and generating a magnetic field in response to passing the electrical signal across the source attached to the media (2), wherein the magnetic field is created in a range of 0.4 to 10 milli gauss; and modulate brain activity based on the generated magnetic field, wherein the brain activity is monitored using an industry standard electroencephalogram (EEG).

16. The medical device (100) as claimed in claim 15, wherein the plurality of ultra-low magneto-electric fields is in the range of 1 Hz to 900 Hz in 16 bit or 32 bit and 44 KHz to 190 KHz resolution.

17. The medical device (100) as claimed in claim 15, wherein the medical device (100) further comprises:

a media holder top (1), a media holder bottom (7), a media (2), wherein the media (2) is placed between the media holder top (1) and the media holder bottom (7), a side panel ticker (3), a battery holder top (4), a battery holder bottom (6), a battery (5), wherein the battery (5) is placed between the battery holder top (4) and the battery holder bottom (6), a LED (11), a short-range communication module configured to communicate with the electronic device, a USB connector (16), wherein the USB connector (16) is configured to charge the medical device, a button (17), a reset switch for the short-range communication module to wake the medical device (100); and a light indicator used for indicating a charging condition, a low battery condition, a full battery condition, a program file running in the medical device (100) and an active state of the short-range communication module.

* * * * *